United States Patent
Kim et al.

(10) Patent No.: US 7,307,703 B2
(45) Date of Patent: Dec. 11, 2007

(54) METHODS OF DETERMINING AN ETCHING END POINT BASED ON COMPENSATION FOR ETCHING DISTURBANCES

(75) Inventors: Yong-Jin Kim, Gyeonggi-do (KR); Hyun-Kyu Kang, Seoul (KR); Seung-Young Son, Gyeonggi-do (KR); Gyung-Jin Min, Seoul (KR)

(73) Assignee: Samsung Electronics Co., Ltd (KR)

( * ) Notice: Subject to any disclaimer, the term of this patent is extended or adjusted under 35 U.S.C. 154(b) by 402 days.

(21) Appl. No.: 11/015,087

(22) Filed: Dec. 17, 2004

(65) Prior Publication Data

US 2005/0134835 A1    Jun. 23, 2005

(30) Foreign Application Priority Data

Dec. 19, 2003    (KR) ............... 10-2003-0093998

(51) Int. Cl.
    G01N 21/00    (2006.01)
(52) U.S. Cl. .................................................. 356/72
(58) Field of Classification Search .............. None
    See application file for complete search history.

(56) References Cited

U.S. PATENT DOCUMENTS

| 4,491,499 | A | * | 1/1985 | Jerde et al. | ........... | 216/60 |
| 5,322,590 | A | * | 6/1994 | Koshimizu | ............. | 438/9 |
| 6,024,831 | A | * | 2/2000 | Hwang et al. | ......... | 216/59 |
| 6,157,867 | A | * | 12/2000 | Hwang et al. | ......... | 700/121 |
| 6,669,810 | B1 | * | 12/2003 | Miyazaki et al. | ..... | 156/345.1 |
| 6,738,756 | B1 | * | 5/2004 | Brown et al. | ........... | 707/2 |
| 2003/0085198 | A1 | * | 5/2003 | Yi et al. | ............... | 216/60 |

FOREIGN PATENT DOCUMENTS

| JP | 10-261622 | 9/1998 |
| JP | 11-054480 | 2/1999 |
| KR | 20-0262123 | 1/2002 |

* cited by examiner

Primary Examiner—Gregory J. Toatley, Jr.
Assistant Examiner—Jonathan Skovholt
(74) Attorney, Agent, or Firm—Myers Bigel Sibley & Sajovec

(57) ABSTRACT

An etching end point of a plasma etch is determined by defining an etch-stop condition. A layer formed on a substrate is etched using a plasma. A luminous intensity of the plasma is measured to determine a first luminous intensity. The luminous intensity is measured again after a predetermined time to determine a second luminous intensity. A determination is made whether a disturbance occurs. Compensation is applied to the measured luminous intensity if the disturbance occurs. A determination is made whether the measured luminous intensity or the compensated luminous intensity satisfies the etch stop condition.

13 Claims, 8 Drawing Sheets

METHODS OF DETERMINING AN ETCHING END POINT BASED ON COMPENSATION FOR ETCHING DISTURBANCES

RELATED APPLICATION

This application claims the benefit of and priority to Korean Patent Application No. 2003-93998, filed Dec. 19, 2003, the disclosure of which is hereby incorporated herein by reference.

FIELD OF THE INVENTION

The present invention relates generally to integrated circuit devices and methods of fabricating the same and, more particularly, to etching of integrated circuit devices during fabrication and methods of performing the same.

BACKGROUND OF THE INVENTION

An etch process may provide a method for forming a predetermined pattern on a substrate. Thus, an etch process is generally used for fabricating a precision device, such as a semiconductor device that includes fine patterns. Etch processes may be classified into dry etch processes and wet etch processes.

A wet etch is a method of selectively etching a predetermined material layer using a predetermined chemical solution. This method may be relatively productive because a plurality of semiconductor substrates can be simultaneously etched. Wet etching, however, may be less desirable when forming fine patterns due to an isotropy etch characteristic thereof. Thus, wet etching is typically used for a restrictive purpose, such as cleaning before a deposition process or removing polymer generated in a dry etch.

A dry etch may have both isotropy and anisotropy etch characteristics. Because a dry etch generally involves etching a predetermined layer using a plasma, an etched layer or bottom patterns thereunder may be etch-damaged. To reduce etch damage and form patterns having a superior quality, only a target layer is etched and etch damage with respect to the bottom patterns may be reduced. An etching end-point of an etch process, meaning a moment when the etch process should be stopped, is an important variable for accurately controlling the etch process.

In the case that the etching end-point is defined as a moment when the target layer is removed to expose a bottom structure, a method of determining the etching end-point may use an optical characteristic, such as change of index of refraction, reflexibility or luminous intensity of plasma when a bottom structure is exposed.

FIG. 1 is a flow chart that illustrates a conventional method of determining an etching end-point. Referring to FIG. 1, after loading a substrate having a predetermined material layer into an etch chamber (S1), various process conditions are set up for controlling an etch process (S2). The etch process includes an etch end condition for determining the etching end-point. Then, RF power is applied for generating an etch plasma (S3). A luminous intensity of the plasma is measured using predetermined optic equipment arranged outside of the etch chamber (S4). Until the measured luminous intensity satisfies the etch end condition, the luminous intensity is repeatedly measured per a predetermined time interval (S5). If the etch end condition is satisfied, the RF power is cut of and the etch process is stopped (S6). Then, the substrate is unloaded out of the etch chamber (S7).

However, optical characteristics measured by the plasma may be disturbed due to various causes. Thus, this disturbance may distort a determination process with respect to an etching end-point measured on the basis of the optical characteristics. A wrong etching end-point may result in a product failure because an etch process may be imperfectly finished.

SUMMARY OF THE INVENTION

According to some embodiments of the present invention, an etching end point of a plasma etch is determined by defining an etch-stop condition. A layer formed on a substrate is etched using a plasma. A luminous intensity of the plasma is measured to determine a first luminous intensity. The luminous intensity is measured again after a predetermined time to determine a second luminous intensity. A determination is made whether a disturbance occurs. Compensation is applied to the measured luminous intensity if the disturbance occurs. A determination is made whether the measured luminous intensity or the compensated luminous intensity satisfies the etch stop condition.

In other embodiments of the present invention, determining the second luminous intensity, determining whether the disturbance occurs, applying compensation to the measured luminous intensity, and determining whether the measured luminous intensity or the compensated luminous intensity satisfies the etch stop condition are repeatedly performed Until the etch-stop condition is satisfied.

In still other embodiments of the present invention, the etch-stop condition comprises predetermined scales defined by a variation of the compensated luminous intensity or a time variation rate of the compensated luminous intensity.

In still other embodiments of the present invention, determining whether a disturbance occurs comprises comparing a difference between the second luminous intensity and the first luminous intensity with a predetermined standard value.

In still other embodiments of the present invention, applying compensation to the measured luminous intensity comprises providing a compensation value by accumulating a difference between the second luminous intensity and the first luminous intensity when a difference between the first luminous intensity and the second luminous intensity is equal to or greater than the predetermined standard value, subtracting the compensation value from the second luminous intensity and assigning the second luminous intensity as a new value for the first luminous intensity.

In still other embodiments of the present invention, determining whether a disturbance occurs comprises determining whether the disturbance occurs based on movement of plasma etch equipment affecting the measurement of the plasma luminous intensity.

In still other embodiments of the present invention, applying compensation to the measured luminous intensity comprises providing a compensation value by accumulating a difference between the second luminous intensity and the first luminous intensity when the plasma etch equipment is moved, subtracting the compensation value from the second luminous intensity, and assigning the second luminous intensity as a new value for the first luminous intensity.

BRIEF DESCRIPTION OF THE DRAWINGS

Other features of the present invention will be more readily understood from the following detailed description of specific embodiments thereof when read in conjunction with the accompanying drawings, in which.

DETAILED DESCRIPTION OF PREFERRED EMBODIMENTS

Figure 1:
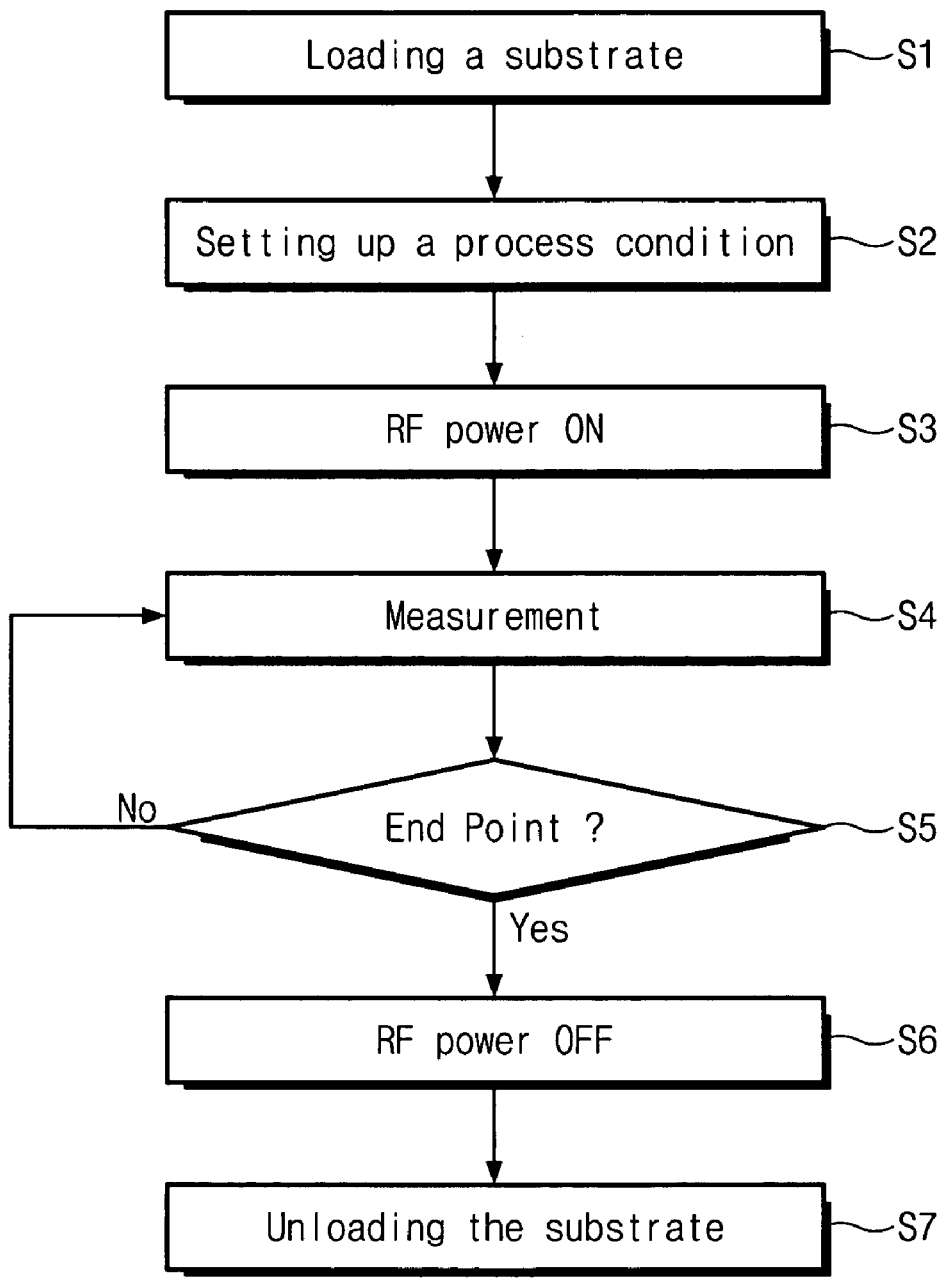
FIG. 1 is a flow chart that illustrates a conventional method of determining an etching end-point.

While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention as defined by the claims. Like reference numbers signify like elements throughout the description of the figures.

It will be understood that when an element or layer is referred to as being "on," "connected to," or "coupled to" another element or layer, it can be directly on, connected, or coupled to the other element or layer or intervening elements or layers may be present. In contrast, when an element is referred to as being "directly on," "directly connected to," or "directly coupled to" another element or layer, there are no intervening elements or layers present. As used herein, the term "and/or" includes any and all combinations of one or more of the associated listed items. Like numbers refer to like elements throughout the description.

It will be understood that although the terms first and second are used herein to describe various regions, layers and/or sections, these regions, layers and/or sections should not be limited by these terms. These terms are only used to distinguish one region, layer or section from another region, layer or section. Thus, a first region, layer or section discussed below could be termed a second region, layer or section, and similarly, a second region, layer or section may be termed a first region, layer or section without departing from the teachings of the present invention.

Furthermore, relative terms, such as "lower" or "bottom" and "upper" or "top" may be used herein to describe one element's relationship to another element as illustrated in the figures. It will be understood that relative terms are intended to encompass different orientations of the device in addition to the orientation depicted in the figures. For example, if the device in the figures is turned over, elements described as being on the "lower" side of other elements would then be oriented on "upper" sides of the other elements. The exemplary term "lower" can, therefore, encompass both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 2:
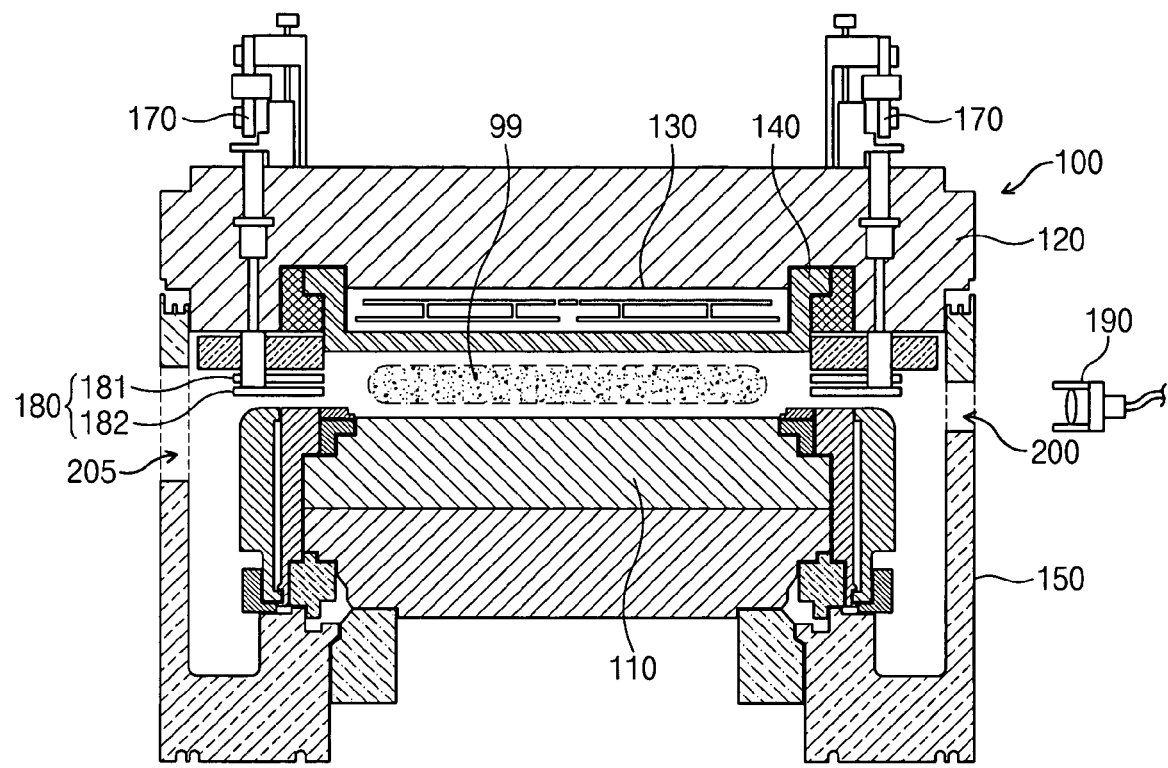
FIG. 2 is a cross-sectional view that illustrates a structure of plasma etch equipment in accordance with some embodiments of the present invention.

FIG. 2 is a cross-sectional view that illustrates a structure of plasma etch equipment in accordance with some embodiments of the present invention. Referring to FIG. 2, plasma etch equipment 100 includes a chuck 110, which is a holder where a substrate is loaded during an etch process. The chuck 110 may use various chucking techniques, such as using electrostatic force, mechanical force, clamping force, and/or vacuum force, in accordance with various embodiments of the present invention. For the etch process, RF power having a predetermined frequency, for example, ranging from about 2 MHz to about 27 MHz, may be applied to the chuck 110.

An upper housing 120 is arranged over the chuck 110, and an upper electrode 140 and a baffle 130 are attached under the upper housing 120. Process gases are supplied between the chuck 110 and the upper electrode 140 through the baffle 130. The supplied process gases are ionized by the RF power to form an etching plasma 99.

A lower housing 150 that surrounds the chuck 110 is connected under the upper housing 120. The process gases are exhausted out of the etch chamber through a predetermined exhauster disposed between the lower housing 150 and the chuck 110.

A confinement ring 180 may be connected to the upper housing 120 for confining the etching plasma 99. The confinement ring 180 is disposed over a frame of the chuck 10. Consequently, the confinement ring 180 is disposed between an upper region of the chuck 110 and the exhauster. Thus, a process gas pressure at the upper region of the chuck 110 can be controlled by the confinement ring 180. For this control, the confinement ring 180 may include an upper confinement ring 181 and a lower confinement ring 182 that can move up and down. A cam 170 is disposed on the upper housing 120 for moving the lower confinement ring 182 up and down. The up and down movements of the lower confinement ring 182 control the process gas pressure and may improve the etch process.

Windows 200 and 205 are disposed between the upper housing 120 and the lower housing 150 for observing the etching plasma 99. An optical device 190 is disposed out of the window 200 for measuring an optical characteristic of the plasma 99. The optical characteristic of the plasma 99 measured by the optical device 190 is used as data for determining an etching end-point. However, the up and down movements of the lower confinement ring 182 may change a light flux of the plasma 99 projected to the optical device 190, which may distort a precise determination with respect to the etching end-point.

The confinement ring 180 is one example of potentially many causes that may distort precise determinations with respect to the etching end-point. That is, the distortion may occur by various other causes.

Figure 3:
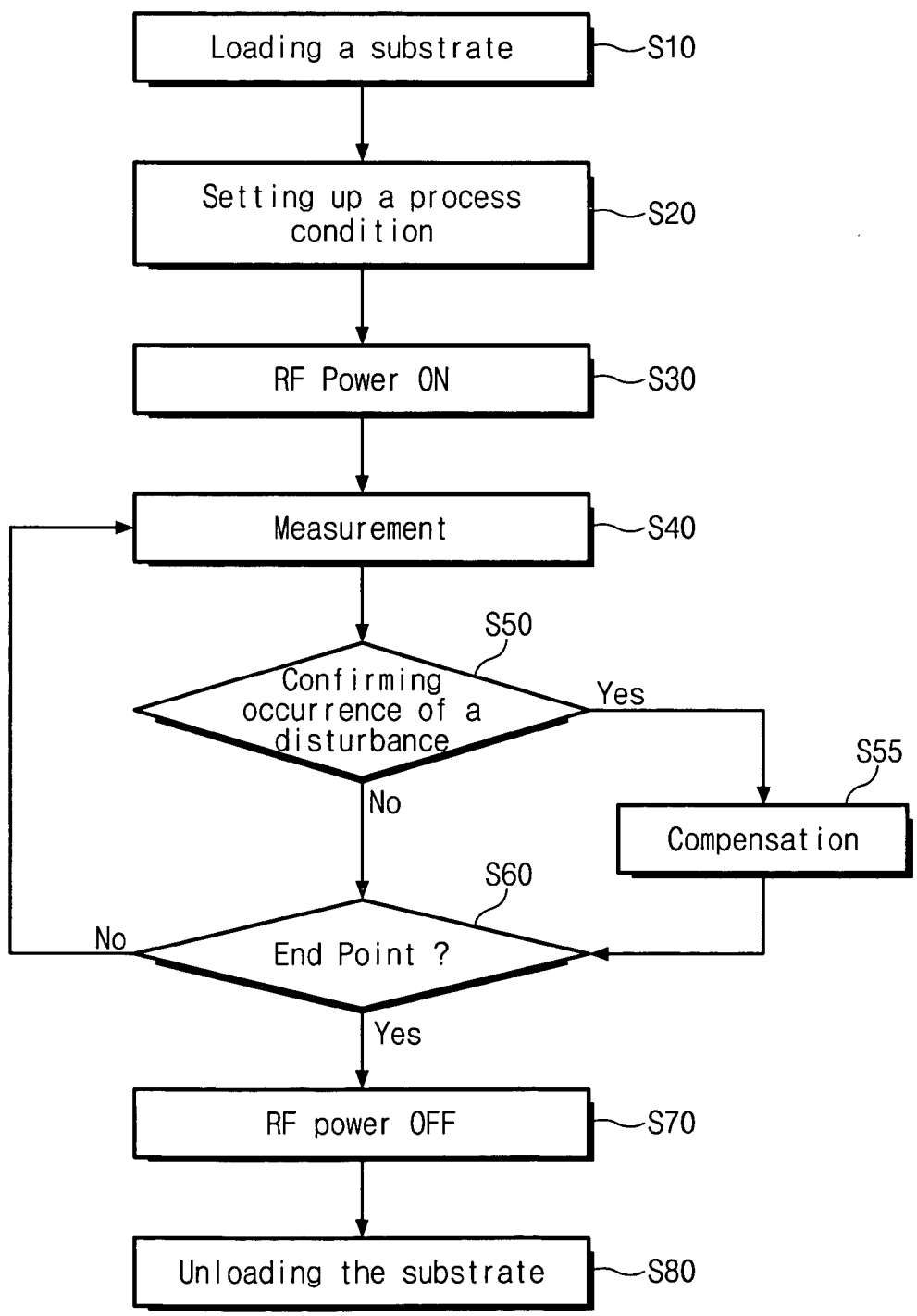
FIG. 3 is a flow chart that illustrates methods of determining an etching end-point by excluding one or more distortion effects according to some embodiments of the present invention.

FIG. 3 is a flow chart that illustrates methods of determining an etching end-point by excluding one or more distortion effects according to some embodiments of the present invention. Referring to FIG. 3, a substrate having a predetermined material layer is loaded into a plasma etch chamber (S10) and various process conditions are set up for controlling an etch process (S20). The process conditions may include a standard value for confirming whether an etch-stop condition is met and a disturbance occurs for determining the etching end-point. Then, the RF power is applied to generate an etching plasma (S30), and a luminous intensity of the plasma is measured (S40). The measured luminous intensity is reported as a value by a predetermined controller that is configured to process data with respect to a plasma luminous intensity. The reported data may be used as a basis for determining an etching end-point and whether a disturbance occurs. A determination is then made whether an abnormal variation of the measured luminous intensity, i.e., a disturbance occurs while the luminous intensity of the plasma is measured (S50). Because the etch-stop condition is determined on the basis of the change of the luminous intensity of the plasma, if a disturbance occurs, the determination with respect to the etching end-point is distorted. Thus, in the case that a disturbance occurs, as illustrated in FIG. 3, an abnormal change of the measured luminous intensity is compensated for (S55). Then, it is determined whether the etch-stop condition is satisfied based on the compensated intensity (S60). Additionally, if a disturbance does not occur, then a determination is made whether the etch-stop condition is satisfied without any compensation applied. Although the disturbance occurs only once in the preceding cycle, the measured luminous intensity may need compensation that corresponds to a cumulative scale of the abnormal change. The compensation due to this accumulative effect will be explained in more details with reference to FIG. 4.

If an etch-stop condition is not satisfied, operations return to block S40 to measure the luminous intensity per a predetermined unit time. Operations of the above-described blocks S40, S50, S55 and S60 are then repeatedly performed. If the etch-stop condition is satisfied, then RF power is cut off and the etch process is terminated (S70). The substrate is then unloaded from the plasma etch chamber (S80).

To not distort the procedure of determining the etching end-point, the disturbance may be classified based on the phenomenon occurring when the etch-stop condition is satisfied. The disturbance may result due to various causes, but generally, the association between a measured result and a cause may be clear or not as explained above with respect to FIG. 2. If the causality is unclear, then occurrence of the disturbance may be determined by analyzing the measured data. If the causality is clear, then occurrence of the disturbance may be determined based on the causality.

Figure 4:
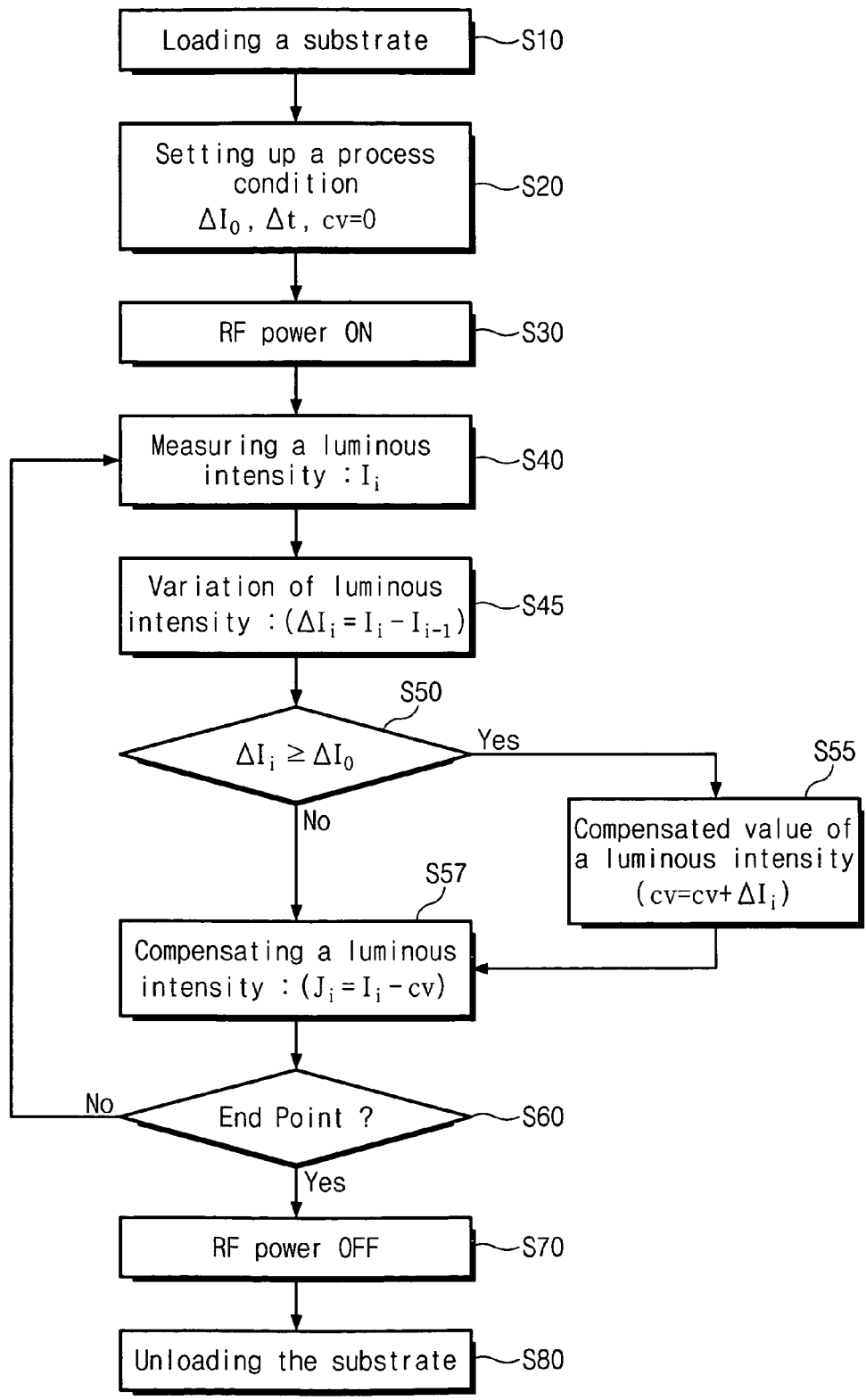
FIG. 4 is a flow chart that illustrates methods of determining an etching end-point and determining the occurrence of a disturbance and compensation therefore in a measured luminous intensity where the causality of the disturbance is unclear in accordance with some embodiments of the present invention.

FIG. 4 is a flow chart that illustrates methods of determining an etching end-point and determining the occurrence of a disturbance and compensation therefore in a measured luminous intensity where the causality of the disturbance is unclear in accordance with some embodiments of the present invention. In the interest of brevity, operations described above with respect to FIG. 3 will be omitted from the description of FIG. 4. Referring to FIG. 4, process conditions are set up (S20), such as, for example, a standard variation $\Delta I_0$ is set up, and a compensation variable cv is initialized (i.e., cv=0). The standard variation is a standard scale of a change of the luminous intensity for determining whether a disturbance occurs or not. The compensation variable is a factor to compensate an accumulative scale of the abnormal change. RF power is then applied to generate a plasma (S30) and a luminous intensity of the generated plasma is measured (S40).

As explained above, the luminous intensities of the plasma are repeatedly measured per a predetermined unit time $\Delta t_0$ and reported (S40). Out of the reported data of the luminous intensities, if an i-th luminous intensity is represented as $I_i$ (i=1~n, wherein n is a case when the etch-stop condition is satisfied.), $I_i-I_{i-1}$ indicates a change between the successively measured luminous intensities, i.e., a variation of intensity $\Delta I_i$.

According to some embodiments of the present invention, a determination with respect to occurrence of a disturbance comprises comparing the variation of intensity $\Delta I_i$ to the standard variation $\Delta I_0$. If the variation of intensity $\Delta I_i$ is higher than the standard variation $\Delta I_0$, then the i-th luminous intensity is interpreted as an abnormal change induced by the disturbance. This interpretation may be correct when a scale of the standard variation $\Delta I_0$ is properly set up. These operations will be described in more detail with respect to FIG. 7, which illustrates data with respect to the reported luminous intensity measured per a predetermined unit time.

Figure 7:
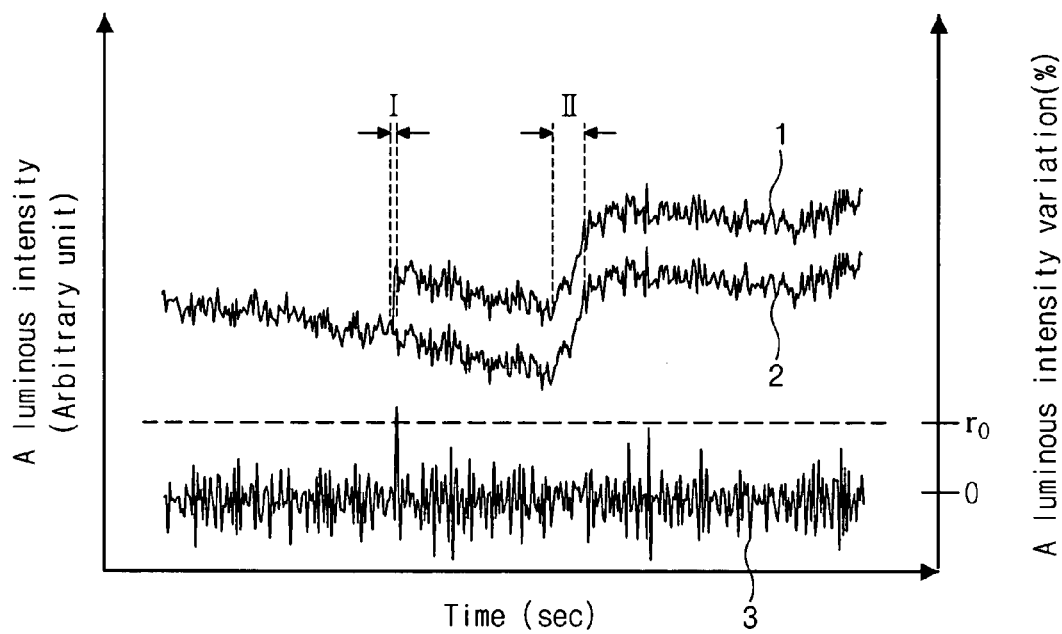
FIG. 7 illustrates data with respect to the reported luminous intensity measured per a predetermined unit time in accordance with some embodiments of the present invention.

Referring to FIG. 7, the luminous intensity is measured per a predetermined unit time $\Delta t_0$ (for example, 200 msec). A broken line graph, indicated by a reference number 1, represents data of the measured luminous intensity without compensation. Another broken line graph, indicated by a reference number 2, represents compensated luminous intensity data. The compensation may be performed by ignoring the change of the luminous intensity at a moment I when a disturbance occurs in accordance with some embodiments of the present invention. Thus, after the moment I, the graph 2 is substantially identical with a horizontally-moved result of the graph 1. A broken line graph, indicated by reference number 3, represents a variation ratio $((I_i-I_{i-1})/(I_i+I_{i-1}))$ of the i-th luminous intensity Ii and a luminous intensity $I_{i-1}$ measured in a previous period, i.e., a variation rate $r_i$ of the luminous intensity.

Figure 5:
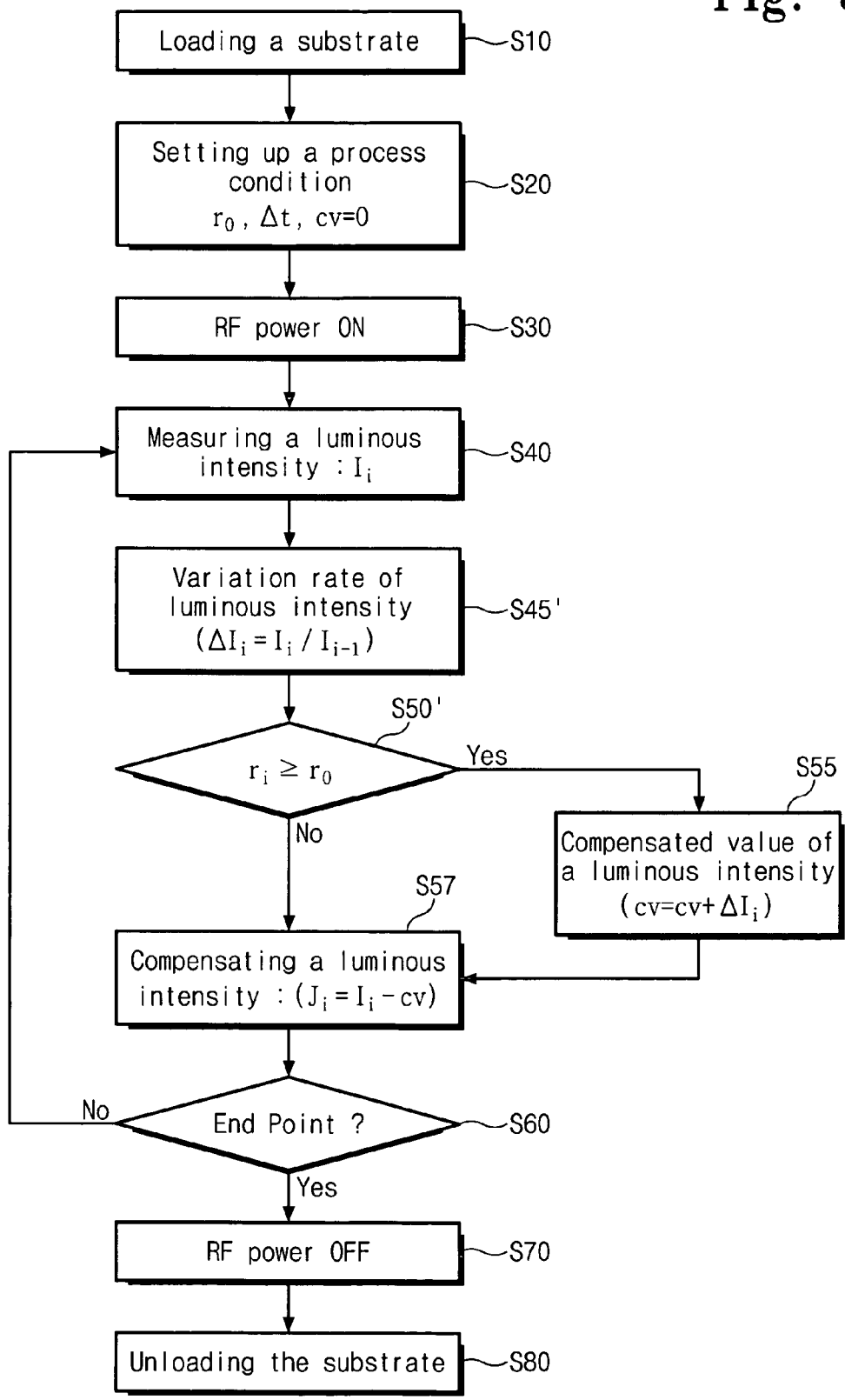
FIG. 5 is a flow chart that illustrates methods of determining an etching end-point and determining the occurrence of a disturbance based on the variation rate of the luminous intensity in accordance with some embodiments of the present invention.

In FIG. 7, a reference number II indicates an etching end-point when the etch-stop condition is satisfied. The variation rate $r_i$ of the luminous intensity changes suddenly at the moment I but smoothly at the moment II. As a result, in graph 3, the variation rate $r_i$ of the luminous intensity is larger than a predetermined standard variation rate $r_0$ at the moment I. In this example, the standard variation rate was 0.3%. Thus, the determination with respect to occurrence of the disturbance can be performed on the standard of the variation rate $r_i$ of the luminous intensity as illustrated in FIG. 5.

A moment when a difference between two successively measured luminous intensities becomes larger than a predetermined standard variation $\Delta I_0$ can be regarded as a moment of occurrence of the disturbance in accordance with some embodiments of the present invention, described above with respect to FIG. 4. In other embodiments of the present invention, a standard of determination may be a ratio or difference.

Consequently, to determine the occurrence of a disturbance, the unit time $\Delta t_0$ and the standard variation rate $r_0$ of the luminous intensity or the unit time $\Delta t_0$ and the standard variation $\Delta I_0$ may be set up to have proper scales. The scales are affected by various process conditions and can be determined by experience.

Referring again to FIG. 4, if a disturbance occurs, compensation is performed (S55) by ignoring the change of the abnormal luminous intensity at the moment I when the disturbance occurs. Particularly, if the disturbance occurs several times, the etching end-point may be determined based on data that excludes the effects of all disturbances. Thus, compensation values for compensating effects according to the disturbance may be accumulated (S55). Additionally, although there was no disturbance in the i-th measurement, if disturbances have occurred for first through (i-1)-th cyclic periods, the i-th luminous intensity may be compensated by the compensated value cv (S57). At this time, the compensated luminous intensity $J_i$ is equal to $I_i$-cv.

Subsequently, until the compensated or measured luminous intensity satisfies the previously set-up etch-stop condition, the operations of blocks S40 through S60 are repeatedly performed. If the etch-stop condition is satisfied, the RF power is cut off and the etch process is stopped (S70). Then, the substrate is unloaded from the plasma etch chamber (S80).

FIG. 5 is a flow chart that illustrates methods of determining an etching end-point and determining the occurrence of a disturbance based on the variation rate of the luminous intensity as discussed above with respect to FIG. 7 (blocks S45' and S50') in accordance with some embodiments of the present invention. In the interest of brevity, operations described above with respect to FIG. 4 will be omitted from the description of FIG. 5.

Figure 6:
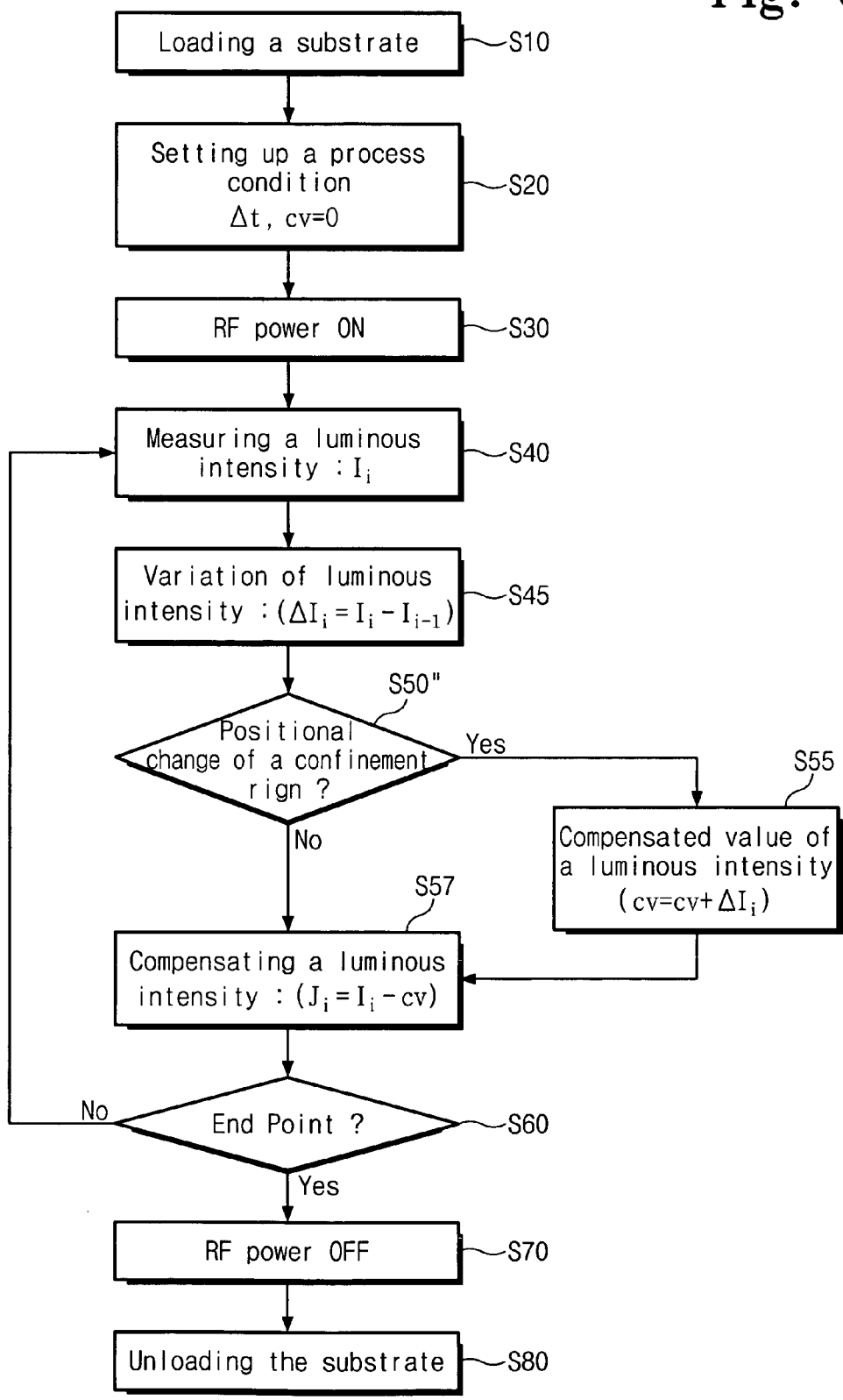
FIG. 6 is a flow chart that illustrates methods of determining an etching end-point and determining the occurrence of a disturbance and compensation therefore in a measured luminous intensity where the causality of the disturbance is clear in accordance with some embodiments of the present invention.

FIG. 6 is a flow chart that illustrates methods of determining an etching end-point and determining the occurrence of a disturbance and compensation therefore in a measured luminous intensity where the causality of the disturbance is clear in accordance with some embodiments of the present invention. In the interest of brevity, operations described above will be omitted from the description of FIG. 6. Referring to FIG. 6, if the causality of the disturbance is clear, the luminous intensity data for determining the etching end-point can be compensated for by monitoring whether a phenomenon causing the disturbance occurs or not. For example, as explained in FIG. 2, the up and down movements of the confinement ring 180 may cause an abnormal change of a plasma luminous intensity. This abnormal change can be compensated for by ignoring the luminous intensity measured when the position of the confinement ring 180 is changed.

Figure 8:
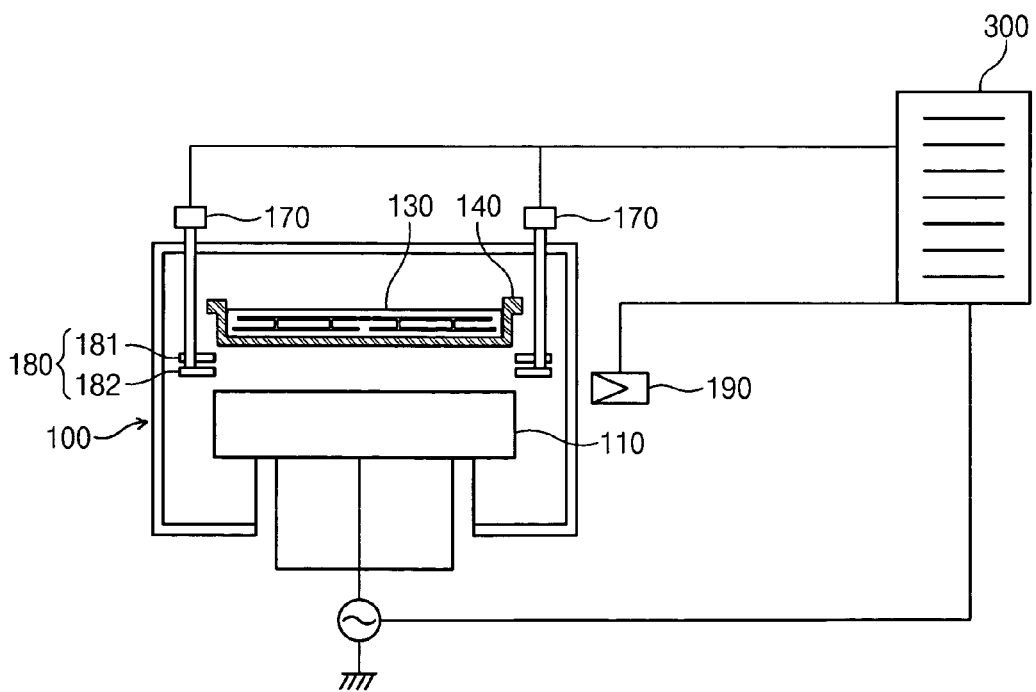
FIG. 8 is a diagram that illustrates plasma etch equipment for determining an etching end point in accordance with further embodiments of the present invention.

For this compensation, as illustrated in FIG. 8, a predetermined control device 300 may synchronously control the confinement ring 180 and the optical device 190. For this, the control device 300 may be electronically connected to the optical device 190 and the cam 170 which is a driving device of the confinement ring 180. Additionally, the control device 300 may be an electronic numerical control device having functions of storing, compensating, and comparing the data of the plasma luminous intensities. In this case, whether the disturbance occurs or not can be determined by monitoring whether the positions of the cam 170 and the confinement ring 180 are changed (S50").

Figure 9:
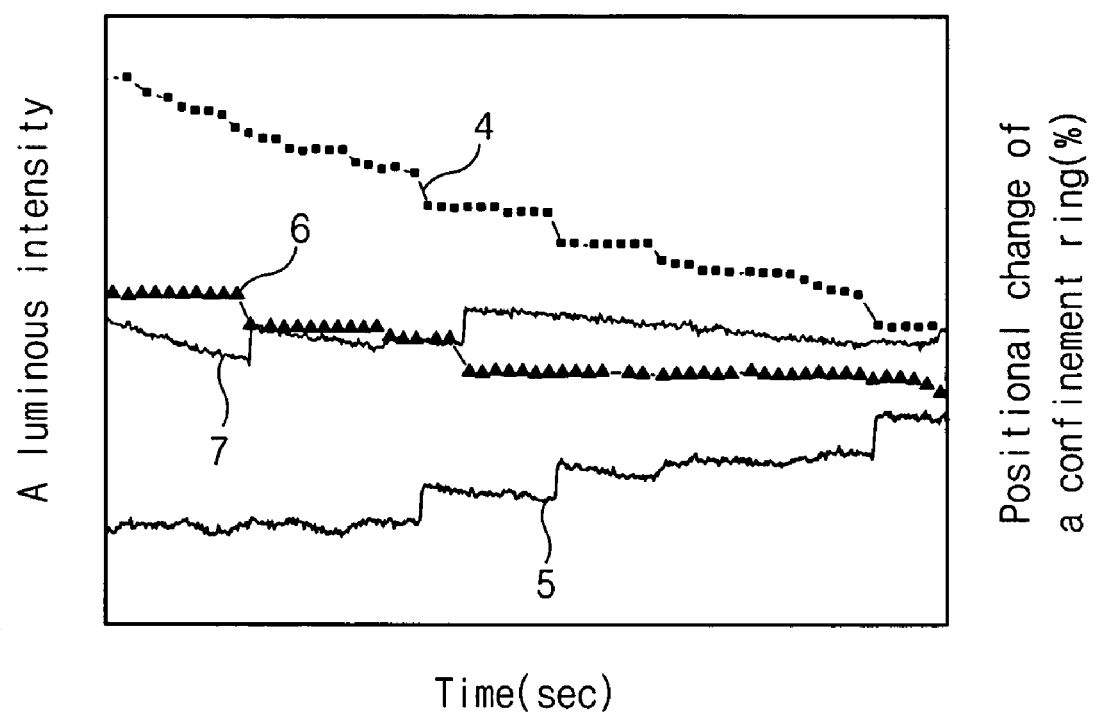
FIG. 9 is a graph that illustrates the relationship between a positional change of a confinement ring and a measured luminous intensity in accordance with some embodiments of the present invention.

FIG. 9 is a graph that illustrates the relationship between a positional change of a confinement ring and a measured luminous intensity in accordance with some embodiments of the present invention. As shown in FIG. 9, two graphs, indicated by reference numbers 4 and 6, respectively, represent positions of the confinement ring 180. Two graphs, indicated by reference numbers 5 and 7, respectively, represent measured luminous intensities. As illustrated, graphs 4 and 5 are almost symmetrical, and graphs 6 and 7 are almost symmetrical. Thus, the measured plasma luminous intensity is dependent on the positional change of the confinement ring 180. Consequently, in the case of the device illustrated in FIG. 8, like FIG. 6, it may be possible to determine whether the compensation operation of block S55 should be performed or not based on a positional change of the confinement ring 180.

According to some embodiments of the present invention, before determining an etching end-point, a method of compensating for a change induced by a disturbance may be performed. Thus, the etching end-point can be determined based on the standard of a measured result in which an effect of an abnormal change induced by a disturbance is removed. As a result, wrong determinations with respect to the etching end-point may be avoided to thereby produce superior products.

In concluding the detailed description, it should be noted that many variations and modifications can be made to the preferred embodiments without substantially departing from the principles of the present invention. All such variations and modifications are intended to be included herein within the scope of the present invention, as set forth in the following claims.

That which is claimed:

1. A method of determining an etching-end point of a plasma etch, comprising:

defining an etch-stop condition;

etching a layer formed on a substrate using a plasma;

measuring a luminous intensity of the plasma to determine a first luminous intensity;

measuring the luminous intensity again after a predetermined time to determine a second luminous intensity;

determining whether a disturbance occurs;

providing a compensated luminous intensity by applying compensation to the measured luminous intensity if the disturbance occurs; and determining whether the measured luminous intensity or the compensated luminous intensity satisfies the etch stop condition.

2. The method of claim 1, wherein determining the second luminous intensity, determining whether the disturbance occurs, applying compensation to the measured luminous intensity, and determining whether the measured luminous intensity or the compensated luminous intensity satisfies the etch stop condition are repeatedly performed until the etch-stop condition is satisfied.

3. The method claim 1, wherein the etch-stop condition comprises predetermined scales defined by a variation of the compensated luminous intensity or a time variation rate of the compensated luminous intensity.

4. The method of claim 1, wherein the determining whether a disturbance occurs comprises comparing a difference between the second luminous intensity and the first luminous intensity with a predetermined standard value.

5. The method of claim 4, wherein applying compensation to the measured luminous intensity comprises:
   providing a compensation value by accumulating a difference between the second luminous intensity and the first luminous intensity when a difference between the first luminous intensity and the second luminous intensity is equal to or greater than the predetermined standard value;
   providing a compensated luminous intensity by subtracting the compensation value from the second luminous intensity; and
   assigning the second luminous intensity as a new value for the first luminous intensity.

6. The method of claim 1, wherein determining whether a disturbance occurs comprises determining whether the disturbance occurs based on movement of plasma etch equipment affecting the measurement of the plasma luminous intensity.

7. The method of claim 6, wherein applying compensation to the measured luminous intensity comprises:
   providing a compensation value by accumulating a difference between the second luminous intensity and the first luminous intensity when the plasma etch equipment is moved;
   subtracting the compensation value from the second luminous intensity; and
   assigning the second luminous intensity as a new value for the first luminous intensity.

8. A method determining an etching-end point of a plasma etch, comprising:
   defining an etch-stop condition and a standard value;
   etching a layer formed on a substrate using a plasma;
   measuring a luminous intensity of the plasma to determine a first luminous intensity;
   measuring the luminous intensity again after a predetermined time to determine a second luminous intensity;
   providing a compensation value by accumulating a difference between the second luminous intensity and the first luminous intensity when a difference between the first luminous intensity and the second luminous intensity is equal to or greater than the standard value;
   providing a compensated luminous intensity by subtracting the compensation value from the second luminous intensity;
   assigning the second luminous intensity as a new value for the first luminous intensity; and
   determining whether the compensated luminous intensity satisfies the etch stop condition.

9. The method of claim 8, wherein determining the second luminous intensity, providing the compensation value, subtracting the compensation value, assigning the second luminous intensity, and determining whether the compensated luminous intensity satisfies the etch stop condition are repeatedly performed until the etch stop condition is satisfied.

10. The method of claim 8, wherein the etch-stop condition comprises a defined variation of the compensated luminous intensity or a time variation rate of the compensated luminous intensity.

11. The method of claim 10, wherein the standard value per a predetermined unit time is greater than a time variance of the compensated luminous intensity defining the etch-stop condition.

12. A method determining an etching-end point of a plasma etch, comprising:
   defining an etch-stop condition;
   etching a layer formed on a substrate using a plasma;
   measuring a luminous intensity of the plasma to determine a first luminous intensity;
   measuring the luminous intensity again after a predetermined time to determine a second luminous intensity;
   providing a compensation value by accumulating a difference between the second luminous intensity and the first luminous intensity when a confinement ring of plasma etch equipment is moved;
   providing a compensated luminous intensity by subtracting the compensation value from the second luminous intensity;
   assigning the second luminous intensity as a new value for the first luminous intensity; and
   determining whether the compensated luminous intensity satisfies the etch stop condition.

13. The method of claim 12, wherein determining the second luminous intensity, providing the compensation value, subtracting the compensation value, assigning the second luminous intensity, and determining whether the compensated luminous intensity satisfies the etch stop condition are repeatedly performed until the etch stop condition is satisfied.

* * * * *